(12) United States Patent
Ziegler et al.

(10) Patent No.: US 8,488,739 B2
(45) Date of Patent: Jul. 16, 2013

(54) LINEAR KINEMATICS SYSTEM WITH ROTATABLE TREATMENT HEAD

(75) Inventors: Christian Ziegler, Erlangen (DE); Jörg Franke, Marloffstein (DE); Franz Dirauf, Ebensfeld (DE); Franz Fadler, Hetzles (DE)

(73) Assignee: Siemens Aktiengesellschaft, München (DE)

( * ) Notice: Subject to any disclaimer, the term of this patent is extended or adjusted under 35 U.S.C. 154(b) by 5 days.

(21) Appl. No.: 12/841,417

(22) Filed: Jul. 22, 2010

(65) Prior Publication Data

US 2011/0150186 A1 Jun. 23, 2011

(30) Foreign Application Priority Data

Jul. 22, 2009 (DE) .......................... 10 2009 035 153

(51) Int. Cl.
*A61N 5/10* (2006.01)
(52) U.S. Cl.
USPC .......................................... 378/65; 378/196
(58) Field of Classification Search
USPC .......................................... 378/65, 193–197
See application file for complete search history.

(56) References Cited

U.S. PATENT DOCUMENTS

| 2,793,296 A | 5/1957 | Peterson |
| 2,950,394 A * | 8/1960 | Stava et al. ..................... 378/65 |
| 3,627,250 A | 12/1971 | Pegrum |

FOREIGN PATENT DOCUMENTS

| DE | 1254777 B | 11/1967 |
| GB | 321094 A | 10/1929 |
| WO | 0074779 A1 | 12/2000 |
| WO | 2007/042440 A1 | 4/2007 |
| WO | 2009/005556 A1 | 1/2009 |

OTHER PUBLICATIONS

International Search Report and Written Opinion, PCT/EP2010/004492, dated Oct. 13, 2010.

* cited by examiner

*Primary Examiner* — Courtney Thomas
(74) *Attorney, Agent, or Firm* — Lempia Summerfield Katz LLC

(57) ABSTRACT

A radiotherapy installation is described, with a treatment head which is arranged on a treatment head support and which has an exit port for a beam generated in a beam generator, and with a patient table. The treatment head support is guided on a first rectilinear guide, which is guided on a second rectilinear guide arranged perpendicular to the first rectilinear guide, in order to move the treatment head relative to the patient table during the radiotherapy.

19 Claims, 2 Drawing Sheets

LINEAR KINEMATICS SYSTEM WITH ROTATABLE TREATMENT HEAD

This application claims priority from German Patent Application No. 102009035153.1 filed in the German Patent Office on Jul. 22, 2009, the entire content of which is incorporated herein by reference.

The invention relates to a device for a radiotherapy installation.

In radiotherapy, linear accelerators are generally used to irradiate human cancer cells. Accelerated electrons, or the bremsstrahlung (high-energy photons) occurring when the electron beam hits a solid body (target), are utilized to destroy tumor cells. The beam emerging from the treatment head widens in a conical shape from its approximately punctiform source, such that a surface of the patient is irradiated, the so-called irradiation field, which is typically larger than the area that is to be treated. In order to avoid or minimize damage of the surrounding healthy tissue, very thick diaphragms (collimators) made of heavy metal are generally used, which limit the therapy beam to the size of the tumor. In addition to fixed diaphragms, leaf collimators, also called multi-leaf collimators (MLC), are increasingly used for this purpose. In order to ensure an effective treatment of the tumor with minimal side effects, the aim should be to target the highest possible radiation dose in the tumor tissue to be irradiated, as distinct from the adjoining tissue, and to achieve the most precise positioning possible within the radiation field.

The vast majority of radiotherapy installations used around the world have a similar structure with a linear accelerator which, in a gantry (L-shaped frame), can pivot on an orbit about a fixed isocenter (horizontal rotation axis). In combination with a possible rotation of the patient table about a vertical axis passing through the fixed isocenter, the tumor, which has been positioned as stationary as possible in the isocenter, can be irradiated from every angle. The radiation dose for the tumor, which remains positioned in the isocenter, is generally applied from several different angles of the gantry and/or of the patient table, such that the dose accumulates in the tumor tissue, while the surrounding healthy tissue receives only a fraction of the total dose.

In addition to the abovementioned and widely used radiotherapy installations with an L-shaped gantry, a number of radiotherapy installations are available which afford some advantages in certain types of treatment. However, design-related disadvantages in each case have to be taken into account.

For some time now, there has been a tomographic structure in which the kinematics of the radiotherapy installation are comparable to those of a diagnostic computed tomography apparatus. The radiation source is in this case arranged inside the annular housing and, during treatment, rotates around the tumor tissue which is to be irradiated and which is positioned in the central opening on the rotation axis. The therapy beam is limited by a slit diaphragm to a very narrow area in the rotation plane, which entails a reduction in the dose rate that can be applied. The dose distribution is influenced by movable elements, by means of individual angle segments of the radiation field being dynamically opened or closed. In addition to the low dose rate that can be applied, and the consequently long irradiation time, a particular disadvantage of the structure is the limitation in terms of the possible directions of irradiation, since the patient table cannot be rotated, or can be rotated only to a very limited extent, about a vertical axis.

There is also a therapy installation structure in which the linear accelerator is positioned by means of an articulated robot arm from the field of industrial manufacturing (WO 2009/005556). The system is suitable in particular for the stereotactic irradiation of small target volumes, primarily in the neuron range. By virtue of the many degrees of freedom of the robot, the radiation source can be positioned and oriented in a very flexible manner relative to the target volume. However, the volume and maximum weight of the beam-generating and beam-shaping components are limited by the structure and the nominal load of the robot, and this limits the possibilities of influencing the therapy beam with the aid of variable diaphragms and filters. The maximum dose rate that can be produced is also limited by this. For these reasons, the installation is generally used only as a supplementary apparatus within an existing radiotherapy department using other radiotherapy installations.

The problem addressed by the invention is that of designing an improved radiotherapy installation having expanded functionality compared to the prior art.

This problem is solved, according to the invention, by the subject matter of claim 1. The radiotherapy installation has at least two rectilinear guides which span one plane of movement and with which the treatment head support, and the treatment head connected thereto, can be positioned or moved in a flexible manner relative to a patient table. The rectilinear guides are advantageously arranged perpendicular to each other, although this is not absolutely essential for achieving the intended purpose. With the beam exit port of the treatment head, connected to the treatment head support, being positioned relative to a predetermined irradiation point, the so-called isocenter, it is possible to use a spatially fixed isocenter, as is customary in most radiotherapy installations, or also a movable isocenter, sometimes determined by geometrical calculation. If the two axes are able to be positioned independently of each other by means of suitable control software and electronics and by means of sufficiently dimensioned drives, it is possible not only to cover simple circular movements around the isocenter but also any desired relative positions and complex trajectories such as ellipses or splines, even with respect to what can be a constantly movable isocenter. In order to orient the beam in the direction of the fixed or movable isocenter, the kinematics system is supplemented by at least one rotation axis which is preferably arranged perpendicular to the plane spanned by the rectilinear guides. To be able to turn the irradiation cross section, shaped in most cases by means of (leaf) collimators, it is advantageous to include a further rotation axis with which the treatment head or the important beam-shaping components contained therein can be rotated about the beam axis. For the positioning and possible orientation of the patient couch or of the tumor tissue relative to the treatment head, the radiotherapy installation is combined with a patient table having additional degrees of freedom. This patient table can preferably have four to six degrees of freedom.

For certain types of treatment described below, it can be advantageous to supplement the described kinematics system with additional axes in order to orient the radiation source. The kinematics system can be supplemented with a further rectilinear guide, which is advantageously perpendicular to the two other rectilinear guides, and/or can be supplemented with at least one further rotary degree of freedom, such that the beam can be positioned and oriented in all six degrees of freedom relative to the isocenter. A rotation axis can be included with which a rotation of the treatment head can be effected about an axis which lies parallel to the movement surface of the first two rectilinear guides and which is at the same time perpendicular to the beam direction. The rotary degree of freedom of the patient table about the vertical axis could also be replaced or supplemented by a rotation axis by means of which the whole positioning kinematics system of the treatment head can be rotated about the isocenter.

In order to avoid a collision of the emitter housing or of the movable kinematics components with the floor and to extend the frequently utilized range of movement, particularly upon rotation about the isocenter, it can be advantageous to provide an eccentricity between the rotation axis (in FIG. 1: 14y) and the preferably parallel axis through the beam exit point—at the target. In this way, the axis path lengths of the linear axes necessary for the irradiation movements can be reduced and/or the mostly used range of movement can be increased with the same axis length.

If the novel positioning kinematics system for the treatment head is combined with a patient table, as is customary in combination with the L-shaped gantry systems, having generally three Cartesian positioning possibilities and at least one degree of freedom (about the vertical axis) or a maximum of three rotary degrees of freedom, it is possible in principle for all irradiation cases that can be irradiated with the L-shaped gantry to be covered also by the radiotherapy installation, at the same time with added advantages. In the case of a positioning kinematics system for the treatment head having additional axes for up to six degrees of freedom, the degrees of freedom of the patient table can optionally be reduced.

In irradiation of the female breast, the free positioning of the treatment head advantageously means that the desired distance between treatment head and isocenter and the exact angle of incidence can be adjusted such that the central beam, in which the dose rate is maximal, is located in the isocenter and, at the same time, by means of the tangential incidence, the adjacent lung tissue can be protected. In the case of the L-shaped gantry structure, this is not possible because of the inflexible positioning and orientation, and, in the robot-based system, it is not possible because of the insufficient size of the irradiation field and the insufficient collimatability of the beam.

Since combined actuation of the two mutually perpendicular linear drives and the additional rotary degree of freedom mean that almost any desired paths and path orientations can be described, the installation is able to describe, inter alia, circular paths having, within reasonable limits, freely adjustable radii (variable distance from source to isocenter). By means of smaller radii, a higher dose rate can advantageously be applied and, therefore, the duration of exposure to irradiation can be shortened, which also affords advantages in so-called stereotactic treatments in which, in most cases in a small number of irradiation sessions, a high dose is applied precisely in the tissue to be irradiated. In some cases, it can also be advantageous if the beam source describes a path deviating from the circular shape, for example in the case of obese individuals or in the case of individuals placed with auxiliary equipment protruding from the patient table, for example in order to get to the next irradiation position in optimum time. It is advantageous, among other things for electron irradiation, that the installation, if appropriate with attached auxiliary components (e.g. a tube for guiding the beam from the treatment head to the surface of the human skin), can be brought close to the patient, such that a considerably higher proportion of the generated dose can be applied.

In some cases it can be advantageous that the isocenter, to which the beam is generally oriented during the irradiation, is not spatially fixed but instead can be variable or movable. In this context, the expression "virtual" isocenter is also used. By virtue of the described kinematics system with two rectilinear guides, the isocenter around which the treatment head rotates during standard irradiation can within reason be located freely in the irradiation plane. In combination with a third linear axis lying perpendicular to the two other linear axes, the isocenter can even be free or movable in all three Cartesian degrees of freedom. This affords advantages, for example, in the time-consuming and mostly manual positioning of the patient in the fixed isocenter before irradiation. In the case of a movable isocenter, the person to be irradiated only needs to be placed roughly in position, after which the position of the tumor tissue (virtual or movable isocenter) can be determined by imaging methods and by comparison of the 3D planning data (e.g. on the basis of a CT scan) and can then be irradiated using suitable path control data. The repositioning of the patient, needed in this so-called automatic set-up in three Cartesian directions of movement and if appropriate in the up to three rotary degrees of freedom of orientation, is therefore no longer necessary.

Advantageously, the positioning kinematics system of the treatment head provides additional degrees of freedom, compared to a radiotherapy installation with L-shaped gantry, in order to track a tumor, as is advantageous in particular in the case of lung tumors and prostate tumors, which move during the irradiation, and at the same time it affords the possibility of applying high dose rates with large beam cross sections and complex beam collimation. By means of the above-mentioned possible expansion of the positioning kinematics system of the treatment head with further axes, and therefore further degrees of freedom, it is also possible to track a tumor in all six spatial degrees of freedom. It may also be expedient to combine the degrees of freedom of the positioning kinematics system of the treatment head with further degrees of freedom of the patient table, in order to achieve the desired relative distance and the desired relative orientation to the movable isocenter lying in the tumor. A combination with additional degrees of freedom that can be achieved by means of so-called dynamic (leaf) collimators may also be advantageous for achieving this purpose.

Hitherto, in whole-body irradiation, the so-called translational technique in particular has been distinguished by a generally desirable homogeneous dose distribution being achieved in the body of the irradiated person. In this irradiation technique, the person who is to be irradiated, and who in most cases lies on a slide system, is moved with a defined speed profile through the activated beam and perpendicular to the beam direction. The concept of irradiation by the translational technique can be transposed to the radiotherapy installation according to the invention, such that the patient is advantageously positioned statically and the positioning kinematics system of the treatment head executes the translational movement. For this purpose, for example, the patient can lie on the floor or on the patient table, and the radiation source, oriented downward, travels in a linear movement along the longitudinal axis of the body and thus provides comparatively homogeneous irradiation of the whole body of the person who is to be irradiated. Compared to other radiotherapy installations, this has the advantage that no additional slide system is necessary, and there is therefore no need for time-consuming retrofitting. With known robot-guided systems, whole-body irradiation is impossible because of the described disadvantages.

Reconfiguration and retrofitting of radiotherapy installations, particularly of the L-shaped gantry design and of the tomographic design, to other irradiation applications has hitherto been extremely time-consuming or has been avoided altogether. Manual work is also required in most cases. In the robot-based irradiation system, which in principle has the degrees of freedom required for example for automatic exchange of components, serious limitations in respect of the available volumes and weights for beam-generating and beam-shaping devices mean that only a very limited number of irradiation applications can reasonably be performed. It is often necessary, before irradiation of the next patient (and in some cases even during an irradiation session), for special beam-shaping and beam-screening components or additional auxiliaries to be mounted or changed, for example, at the beam exit of the therapy appliance (e.g. special collimators for stereotactic irradiation, or tubes for electron irradiation). With the positioning kinematics system of the treatment head, it is possible to adopt positions and orientations that are very advantageous when working on the appliance. Thus, for example, it is possible to adopt ergonomic positions for exchange of components and for maintenance, such that radiology assistants or technical personnel are able to work on the relevant parts of the installation in suitable positions, which can be ergonomically adapted on an individual basis. Parking positions can also be adopted (e.g. when a radiology assistant enters the bunker), such that, for example, the radiology assistant can get to the patient easily. In addition, an automatic exchange of collimators, beam-shaping components, auxiliaries, imaging components, etc., is conceivable, such that the machine automatically brings forward the component assigned to the particular irradiation case and mounts the component on the appliance, for example by means of a quick coupling (comparable to a gripper exchange system in industrial handling machines). For this purpose, the components can be kept ready in a magazine for example, advantageously in the edge area of the work space.

By means of current suitable control software and control electronics and axis components, the paths to be traveled can be planned and controlled so quickly that a high degree of path precision can be expected. For this purpose, all axes can expediently be positioned independently of one another. This affords the possibility of also using dynamic irradiation techniques in which irradiation is performed during the movement and, if appropriate, the collimator leaves, the dose rate and other irradiation parameters can also be adjusted. Another advantage is that, in contrast to the L-shaped gantry (with only one axial degree of freedom), multi-axial calibration routines can also be performed. These can be performed at regular intervals, using suitable software and if appropriate additional calibration aids. In this way, undesired beam deviations following the calibration routine or calibration measurements can be largely eliminated, for example by compensating values stored in the control. A wide variety of calibration methods are part of the prior art and are often used in robotics for example. By suitable integration of sensors and/or collision or path-planning algorithms, the kinematics system can also advantageously be used to execute compensation strategies, for example if there is a threat of a collision with a human, with an auxiliary device, etc.

In order to ensure a time-optimized work sequence on the radiotherapy installation and to be able to adjust all irradiation orientations, the rotation axis (in FIG. 1: 14y) should be able to freely rotate as far as possible in both directions, but should at least be able to provide a 360° rotation. The supply line(s) and signal line(s) for the beam-generating components can advantageously be guided through from the rear of the therapy installation via suitable cable guides (e.g. drag chains) through the bearing ring of the rotary axis or can in some cases be realized through collector rings or rotation through-guides, etc. The embodiment of the illustrated horizontal axis with two parallel transverse beams promotes the possibility of elements being guided from the rear through the bearing ring of the rotation axis to the front, or vice versa. A two-beam construction of this kind would also have the advantage of a greater rigidity against twisting, since heavy components can be judiciously positioned, e.g. as compensating weights.

All in all, it is possible to move some of the heavy beam-generating components through the rotation bearing of the rotation axis (in FIG. 1: 14y) to the rear of the installation and thereby reduce the gravitational bending moment generated by the beam-shaping components and the beam-generating components or distribute said gravitational bending moment uniformly on both sides, such that the center of gravity of the treatment head support with treatment head advantageously lies in the center of the bearing ring of the rotation axis. These components can either be connected fixedly to the treatment head or can also be positioned partially or completely relative thereto. By using a so-called magnetron as high-frequency generator (comparatively compact structure and insensitive to movements/tilts), it is possible, and can be advantageous, to place all the beam-generating and beam-shaping components in the treatment head support and in the treatment head, which permits a reduction in the number of necessary and in some cases expensive add-on components (e.g. omission of the rotary joint for transmitting the high-frequency energy from a stationary part to a movable part of a radiotherapy appliance).

A further advantage of the radiotherapy installation is that it can be produced at comparatively low cost using standard components available on the market. Moreover, since important beam-generating and beam-shaping components (e.g. the multi-leaf collimator and the add-on components attachable thereto or the linear accelerator) can be transposed from conventional radiotherapy installations (in particular the L-shaped gantry construction) without any great expenditure in terms of adaptation, the add-on components, auxiliary devices, etc., that have become established in hospitals can in some cases continue to be used, such that most of the known and established work procedures on the radiotherapy installation can also advantageously be maintained.

The most common integration of imaging and sensing methods (e.g. kV or mV X-ray devices for 2D or 3D imaging, ultrasound, stereoscopic infrared cameras, etc.) for location of the patient, of the tumor, of installation components, of auxiliary devices, etc., spatially or directly on the appliance can also be carried over to the novel system. Thus, for example, by integration of a C-arm (with X-ray source and X-ray detector at the opposite ends of the arm similar to those customary in diagnostic radiology) integrated in the treatment head support or in the treatment head, it is possible to generate 2D or 3D X-ray images, for example to monitor the position of the tumor tissue.

Also possible in principle is the integration of established imaging systems, as in the L-shaped gantry systems obtainable on the market, in a comparable kinematic construction. For this purpose, a web can be secured on the treatment head support, which web is oriented parallel to the beam direction near the kinematic linear axis system on which detector(s) and X-ray source(s) are positioned if appropriate via suitable mechanisms for the imaging (in this connection reference can be made, for example, to the structure described in WO 2007/042440). This would correspond basically to a kind of imitation of the L-shaped gantry structure, but with the additional advantages of the radiotherapy installation. Likewise, the common imaging possibilities offered by other manufacturers, or types which are often based on multi-joint tilting mechanisms and which for the most part tilt the kV source and the kV detector in laterally (X-ray beam direction perpendicular to the MV beam direction) and/or tilt the MV detector in from below (into the beam), can be carried over to the radiotherapy installation. External stationary imaging systems (e.g. with two or three mutually perpendicular kV source/detector pairs), as are offered with stereotactic irradiation systems for example, can also be combined with the radiotherapy installation. It can also be advantageous for autonomous mobile imaging systems, such as are known from radiological diagnostics, to be integrated spatially or directly on the patient table.

Figure 1:
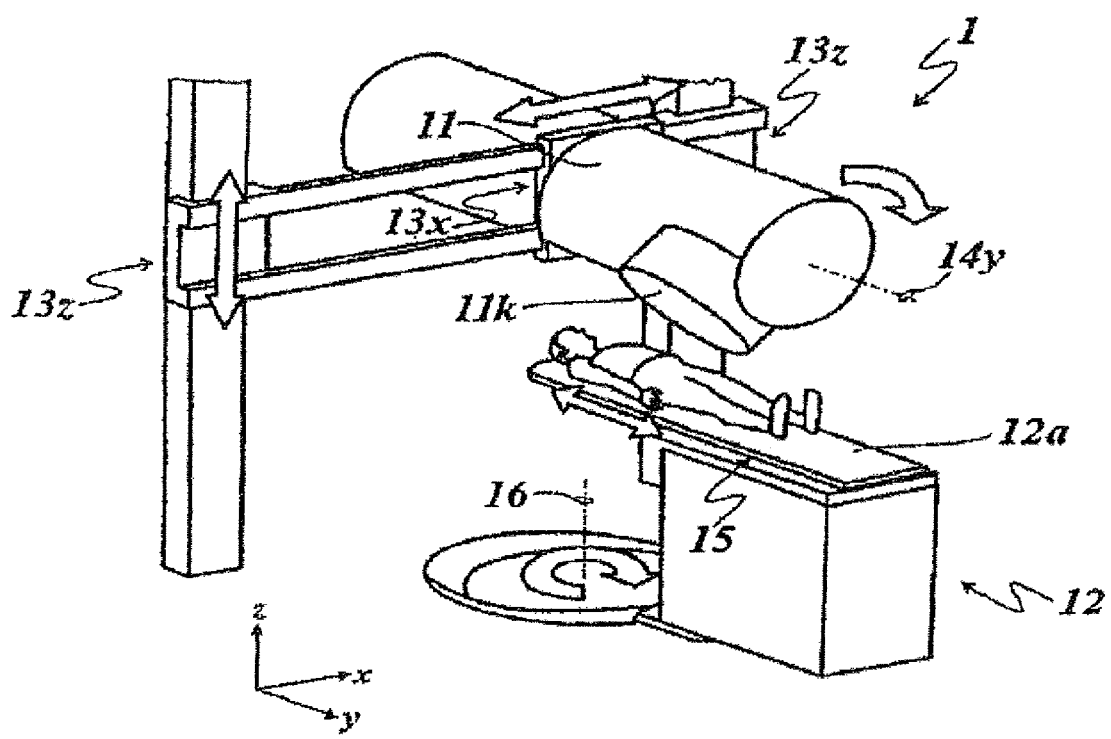
FIG. 1 shows one embodiment of a radiotherapy installation.
Figure 2:
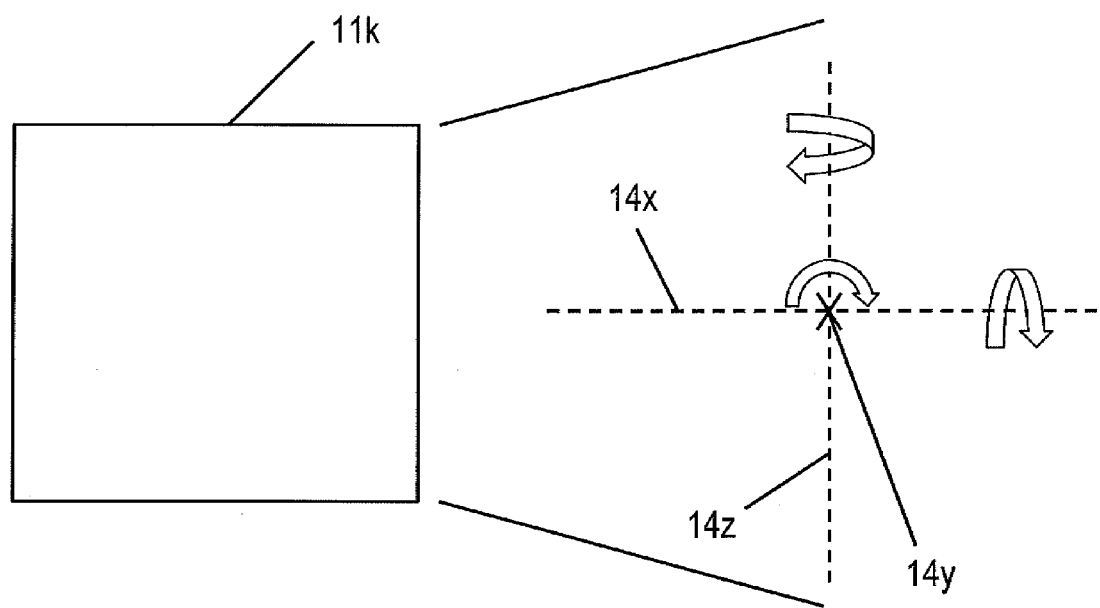
FIG. 2 shows one embodiment of a treatment head.

FIG. 1 shows an example of a radiotherapy installation 1 in which a treatment head support 11 and a treatment head 11k connected to the latter can be positioned relative to a radioparent patient couch 12a via a horizontally arranged first rectilinear guide 13x and a vertically arranged second rectilinear guide 13z arranged perpendicular to the latter. The beam can be generated by means of a linear accelerator and, in order to achieve the intended purpose, the rectilinear guides can also be arranged relative to each other at an angle deviating by a few degrees from 90°. The support structure of the first kinematic axis (second rectilinear guide 13z) is embodied by two stands, which are mounted on the floor and ceiling and on each of which linear slides form the second rectilinear guides 13z. Along two parallel transverse beams mounted on these linear slides, a further linear slide embodies the second axis of the kinematics system (the first rectilinear guide 13x). To ensure that the exit port of the treatment head 11k connected to the treatment head housing can be oriented in all positions with respect to the irradiation center, also called the isocenter, located on the patient couch 12a, a rotation axis 14y is provided. The latter can be embodied by means of a rotary bearing unit secured on the linear slide of the first rectilinear guide 13x. Many of the in some cases very heavy beam-generating components can be fitted in the treatment head support 11 connected to this rotary bearing unit. The heavy components can in this case be placed on both sides of the plane spanned by the first rectilinear guide 13x and the second rectilinear guide 13z. The respective components can in this case be connected to one another through the rotary bearing unit and the transverse beams. A collimator (e.g. multi-leaf collimator) equipped with retractable and extendable leaves and rotatable about the beam axis can be provided in the treatment head 11k, some of the radiation being screened off by said collimator, such that the irradiation cross section can be shaped. In order to ensure that the isocenter, which is not necessarily spatially fixed in the radiotherapy installation 1 and is placed by geometric calculation in the tissue to be irradiated, can be moved relative to the beam exit, the patient couch 12a can be spatially manipulated itself or together with a multi-axis patient table 12. By combination of the four described degrees of freedom of the beam-positioning unit with an additional rectilinear guide 15 of the patient couch and a rotation axis through the fixed isocenter 16, all six relative spatial degrees of freedom between beam exit and isocenter can in principle be adjusted with the radiotherapy installation 1.

The first rectilinear guide 13x and the second rectilinear guide 13z can be driven, for example, by customary electric drives via spindles, chains, toothed racks, etc., and by means of suitable position sensors or can be positioned directly by means of direct drives and guided by means of linear guides. The linear axis components of the second rectilinear guide 13z can in this case be firmly secured on the illustrated support columns or integrated therein. The rotary movement of the rotation axis 14y can be guided, for example, by means of suitable roller bearings, ball bearings, etc., and can be driven, for example, by means of an electric motor via a cylindrical gearing.

The described axes of the radiotherapy installation 1 can be positioned independently of one another by means of suitable control software and electronics. In this way, complex irradiation paths deviating from simple rotary or translatory movements can also be covered in the working range of the radiotherapy installation 1. In addition, further axes can be integrated in the patient table 12 or the patient couch 12a. Further axes can also be integrated in the kinematics set-up for the positioning of the beam (beam-positioning kinematics) in order to be able to provide all six spatial degrees of freedom without the patient couch having to be moved. In addition to the two rectilinear guides arranged perpendicular to each other, a third rectilinear guide can be included, with which the treatment head support 11 and the treatment head 11k can be positioned along an axis extending perpendicular to the two other rectilinear guides. Moreover, a further rotary axis can be included, which permits a rotation of the treatment head 11k about an axis 14x that is perpendicular both to the rotation axis 14y and also to an axis describing the beam direction.

By arranging movable or immovable imaging components (not shown), such as X-ray sources or detectors, on the treatment head support 11 and/or on the treatment head 11k, or by providing external imaging components arranged independently of the kinematics set-up of the radiotherapy installation 1, it is possible to record images of the target volume to be irradiated, and of the surrounding area, and thereby to determine the relative position of the patient couch 12a, or of the tissue to be irradiated and the surrounding tissue, in relation to the beam exit port.

The invention claimed is:

1. A radiotherapy device comprising:
   a treatment head that is arranged on a treatment head support and has an exit port for a beam generated in a beam generator; and
   a patient table,
   wherein the treatment head support is guided on a first rectilinear guide that is guided on a second rectilinear guide arranged perpendicular to the first rectilinear guide such that the treatment head is operable to be moved relative to the patient table during a radiotherapy, and
   wherein the treatment head is indirectly or directly guided on a third rectilinear guide.

2. The radiotherapy device according to claim 1, wherein the beam generator is a linear accelerator.

3. The radiotherapy device according to claim 1, wherein the beam generator is arranged in the treatment head, is arranged in the treatment head support, or is arranged in the treatment head and the treatment head support.

4. The radiotherapy device according to claim 1, wherein the first rectilinear guide is arranged horizontally, and the second rectilinear guide is arranged vertically.

5. The radiotherapy device according to claim 1, wherein the first rectilinear guide is guided on two parallel second rectilinear guides spaced apart from each other, the two parallel second rectilinear guides comprising second rectilinear guide, or
   wherein the second rectilinear guide is guided on two parallel first rectilinear guides spaced apart from each other, the two parallel first rectilinear guides comprising first guide.

6. The radiotherapy device according to claim 1, wherein the third rectilinear guide is arranged horizontally.

7. The radiotherapy device according to claim 1, wherein the treatment head is mounted rotatably about a first rotation axis arranged on the treatment head support perpendicular to guide axes of the first rectilinear guide and the second rectilinear guide.

8. The radiotherapy device according to claim 7, wherein a maximum rotation angle about the first rotation axis is greater than or equal to 360°.

9. The radiotherapy device according to claim 7, wherein the first rotation axis is arranged horizontally.

10. The radiotherapy device according to claim 7, wherein the treatment head is also mounted rotatably about a second rotation axis that is arranged parallel to the guide axis of the first rectilinear guide.

11. The radiotherapy device according to claim 10, wherein a maximum rotation angle about the second rotation axis is greater than or equal to 360°.

12. The radiotherapy device according to claim 10, wherein the second rotation axis is arranged horizontally.

13. The radiotherapy device according to claim 10, wherein the treatment head is also mounted rotatably about a third rotation axis that is perpendicular to the first rotation axis and the second rotation axis.

14. The radiotherapy device according to claim 13, wherein a maximum rotation angle about the third rotation axis is greater than or equal to 360°.

15. The radiotherapy device according to claim 13, wherein the third rotation axis is arranged vertically.

16. The radiotherapy device according to claim 13, wherein the treatment head is arranged in a cardan suspension that is connected in a rotationally fixed manner to the treatment head support or vice versa.

17. The radiotherapy device according to claim 1, wherein a patient couch on the patient table or the patient table is guided on a rectilinear guide arranged parallel to a longitudinal axis of the patient table, on a rectilinear guide arranged transverse to the longitudinal axis of the patient table, or on the rectilinear guide arranged parallel to the longitudinal axis of the patient table and on the rectilinear guide arranged transverse to the longitudinal axis of the patient table.

18. The radiotherapy device according to claim 17, wherein the patient table is rotatable about a vertical rotation axis extending through a fixed isocenter.

19. The radiotherapy device according to claim 17, wherein the patient couch is adjustable in height.

* * * * *